United States Patent
Bae et al.

(10) Patent No.: US 9,389,207 B2
(45) Date of Patent: Jul. 12, 2016

(54) PORTABLE GAS ANALYZER

(71) Applicant: Mona L. Shannon, Champaign, IL (US)

(72) Inventors: Byunghoon Bae, Champaign, IL (US); Jihyung Kim, Champaign, IL (US); Mark A. Shannon, Urbana, IL (US); Taekyu Kang, Newark, DE (US); Mona L. Shannon, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 342 days.

(21) Appl. No.: 13/801,949

(22) Filed: Mar. 13, 2013

(65) Prior Publication Data

US 2013/0276512 A1    Oct. 24, 2013

Related U.S. Application Data

(60) Provisional application No. 61/636,151, filed on Apr. 20, 2012, provisional application No. 61/636,116, filed on Apr. 20, 2012.

(51) Int. Cl.
*G01N 30/02* (2006.01)
*G01N 30/68* (2006.01)
*G01N 30/00* (2006.01)

(52) U.S. Cl.
CPC .............. *G01N 30/02* (2013.01); *G01N 30/68* (2013.01); *G01N 2030/0095* (2013.01)

(58) Field of Classification Search
CPC .................. G01N 30/02; G01N 30/68; G01N 2030/0095; G01N 30/6095
USPC ................................................ 73/23.35, 23.4
See application file for complete search history.

(56) References Cited

U.S. PATENT DOCUMENTS

| | | | | |
|---|---|---|---|---|
| 5,611,846 A | * | 3/1997 | Overton | G01N 30/64 73/23.36 |
| 5,741,711 A | * | 4/1998 | Amirav | G01N 30/68 422/54 |
| 5,804,701 A | * | 9/1998 | Berger | G01N 30/30 73/23.42 |
| 6,096,178 A | * | 8/2000 | Amirav | G01N 27/626 204/274 |
| 6,386,014 B1 | * | 5/2002 | Butch | G01N 30/6095 73/23.22 |
| 6,627,454 B2 | * | 9/2003 | Amirav | G01N 30/68 422/89 |
| 7,735,352 B2 | * | 6/2010 | Alm | G01N 30/463 73/23.4 |
| 8,305,086 B2 | * | 11/2012 | Muller | G01N 27/626 324/464 |
| 8,414,832 B1 | * | 4/2013 | Roques | G01N 30/30 422/89 |
| 2013/0186174 A1 | * | 7/2013 | Seo | G01N 30/00 73/23.35 |

OTHER PUBLICATIONS

Amirav, A. et al., "Electrolyzer-Powered Flame Ionization Detector", Analytical Chemistry, vol. 69, No. 6, Mar. 15, 1997, pp. 1248-1255.*
Zimmermann, S. et al., Micro Flame Ionization Detector and Micro Flame Spectrometer, Sensors and Actuators B, vol. 63, 2000, pp. 159-166.*

* cited by examiner

*Primary Examiner* — Daniel S Larkin
(74) *Attorney, Agent, or Firm* — Kilpatrick Townsend & Stockton LLP

(57) ABSTRACT

A portable gas analyzer comprising an integrated micro-flame ionization detector (micro-FID), a micro-gas chromatograph (micro-GC), an electrolyzer, and a flame-shaped electrode are provided. The components of the portable gas analyzer can be integrated into a single "lunchbox" sized housing with all the peripherals required to operate the micro-GC/FID without an external power and gas supply.

27 Claims, 15 Drawing Sheets

PORTABLE GAS ANALYZER

This application claims priority to Application Ser. No. 61/636,151, filed Apr. 20, 2012, and Application Ser. No. 61/636,116, filed Apr. 20, 2012, the contents of which are hereby incorporated by reference in their entirety.

This invention was made, at least in part, with U.S. government support under Grant No. W911NF-10-C-0002 awarded by the U.S. Army. The government has certain rights in the invention.

FIELD OF THE INVENTION

The present subject matter relates to system and apparatus for detecting gaseous analytes. In particular, an integrated hand-portable micro-gas chromatograph (micro GC) and micro-flame ionization detector (micro FID) with a built in electrolysis system for generating oxygen and hydrogen gas are described, as well as an electrode shape that allows for superior flame ionization and improved sensitivity.

BACKGROUND

Detecting contaminants in air is an important consideration in closed environments, such as manned space crafts and the International Space Station (ISS). It is important to constantly keep track of the air quality in manned spacecraft and the ISS for the safety of the crew as well as any experiments on board. The cabin contains a limited resource of breathable air to sustain life. In order to protect the astronauts, this air must be kept clean from hazardous gases. Hazardous gases or vapors from inside and outside the cabin may leak into the air supply and pose a major threat to the crews' health. A real-time gas detector is desired to notify the crew members immediately when the hazardous gases or vapors become present in the cabin air. Currently, contaminates released into the air supply are monitored by frequently analyzing the cabin air using a variety of technologies including Mass Spectrometry (MS), Differential Mobility Spectrometry (DMS), and Flame Ionization Detection. Often, these detection instruments are coupled to a front-end Gas Chromatograph (GC).

The use of standard, dorm refrigerator-sized GC/MS analyzers for planetary missions would be prohibitively expensive, since they are heavy, slow, and require maintenance. A portable gas analyzer can resolve this issue if it is sensitive enough to detect the required species for the mission. It will also provide the crew with real-time information about an unknown environment, rather than waiting for remote data analysis.

Portable gas analyzers can also be useful in a variety of industrial settings, such as manufacturing facilities that use chemical agents for cleaning, etching, dissolving, etc. as part of the manufacturing process. Portable gas analyzers can also be used in military environments, especially in combat situations where the threat of chemical warfare is present, and at airports, subways, or other public facilities to detect minute amounts of chemical agents that might indicate the presence of chemical warfare agents or other hazardous substances.

A Flame Ionization Detector (FID) is a sensitive detector for hydrocarbons. The measurement is performed due to the chemical ionization of the hydrocarbons in an oxy-hydrogen or air-hydrogen flame. The hydrocarbons can be detected by measuring the resulting ion current. The FID has been extensively used in research and industrial labs to analyze gas samples in tandem with gas chromatographs (GC).

However, none of the reported micro-GC/FID systems were truly portable, and there is an ongoing need for portable, sensitive, and self-contained systems capable of accurately analyzing gaseous species in the air.

SUMMARY OF THE INVENTION

Aspects of the present subject matter include, among other objects, a system and apparatus comprising a portable gas analyzer containing a micro-FID and a micro-GC, an integrated electrolysis system for producing oxygen and hydrogen on board the portable gas analyzer, and an electrode design that allows for highly efficient flame ionization with resulting high analytical sensitivity.

In one aspect of the present subject matter, a portable gas analyzer system is provided. The portable gas analyzer system may include a micro gas chromatograph, a micro flame ionization detector, a flame-shaped electrode in the micro flame ionization detector, and a water electrolyzer.

In some embodiments, the electolyzer may provide substantially all of the oxygen and hydrogen for the flame ionization detector.

In some embodiments, the electrolyzer can contain a plurality of gas outlet ports each connected to a desiccant tube.

In some embodiments, the desiccant tube can reduce the humidity of gas from the gas outlet ports to less than 5%.

In some embodiments, the micro gas chromatograph can include a microcolumn having a silicon substrate.

In some embodiments, the micro gas chromatograph can include a preconcentrator.

In some embodiments, the micro flame ionization detector can include a silicon layer.

In some embodiments, the silicon layer is from about 400 to 1000 μm thick.

In some embodiments, the silicon layer is about 750 μm thick.

In some embodiments, the silicon layer can be situated between two quartz plates.

In some embodiments, the microcolumn can include a fusion bonded silicon substrate.

In some embodiments, the silicon layer is from about 400 to 1000 μm thick.

In some embodiments, each of the two silicon plates may include a microchannel.

In some embodiments, at least one of the quartz plates may include an exhaust hole.

In some embodiments, the silicon layer may include an air channel and a hydrogen channel.

In some embodiments, the angle between the air channel and the hydrogen channel is about 150°.

In some embodiments, the flame-shaped electrode may be situated on both quartz plates.

In some embodiments, the dimensions of the flame-shaped electrode substantially conform to dimensions of a flame in provided by the micro-flame ionization detector.

According to further aspects of the present subject matter, a portable gas analyzer system may be provided including a micro gas chromatograph, a micro flame ionization detector, at least one thermal isolation barrier disposed between the chromatograph and the ionization detector; and a water electrolyzer.

In some embodiments, the isolation barrier can include a high-temperature polymer.

In some embodiments, the isolation barrier can include a hollow chamber.

In some embodiments, the hollow chamber can be filled with air.

In some embodiments, the hollow chamber can be coated with a reflective metal.

In some embodiments, the ionization detector contains a flame-shaped electrode.

In some embodiments, the isolation barrier can include a frame support structure.

In some embodiments, the isolation barrier can include one or more fluid ports.

In some embodiments, the portable gas analyzer system may include at least one additional component selected from the group consisting of a micro-flame ionization detector, a micro gas chromatograph, a micro thermal conductivity detector, wherein the at least one additional component is separated from the flame ionization detector or gas chromatograph by the at least one thermal isolation barrier, and wherein the at least one additional component is independently replaceable.

According to further aspects of the present subject matter, a method may be provided including one or more steps of providing a sample of gas, and injecting the sample of gas into a portable gas analyzer, wherein the portable gas analyzer comprises: a micro gas chromatograph, a micro flame ionization detector, a flame-shaped electrode in the micro flame ionization detector, and a water electrolyzer. Embodiments may also include separating the sample of gas into analyzable portions, ionizing the analyzable portions in the ionization detector with the flame-shaped electrode, and obtaining analysis results.

DETAILED DESCRIPTION

Figure 1:
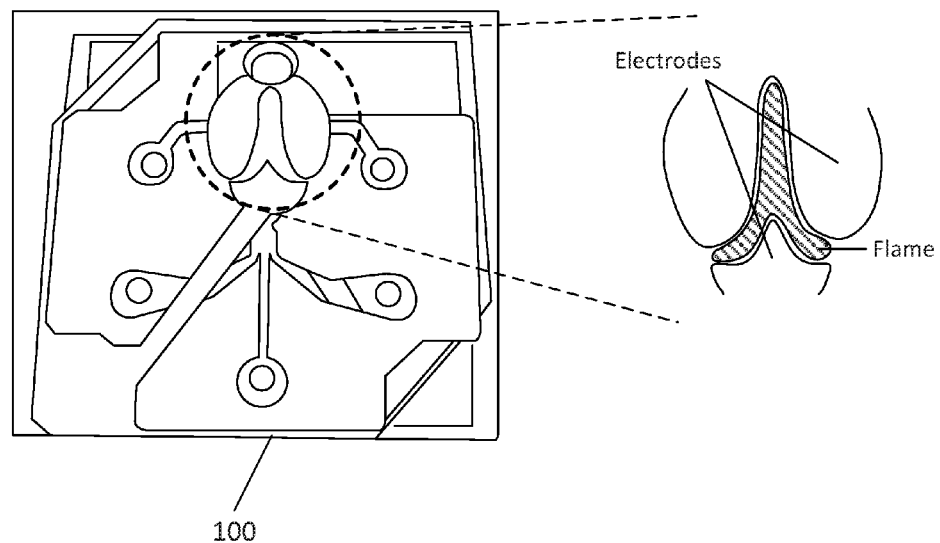
FIG. 1 shows an electrode design for a flame shaped electrode.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law.

Moreover, it is noted that like reference numerals represent similar parts throughout the several views of the drawings. It is understood that the invention is not limited to the particular methodology, protocols, devices, apparatus, materials, and reagents, etc., described herein, as these may vary. It is also to be understood that the terminology used herein is used for the purpose of describing particular embodiments only, and is not intended to limit the scope of the invention. It must be noted that as used herein and in the appended claims, the singular forms "a," "an," and "the" include plural reference unless the context clearly dictates otherwise.

In one embodiment, the portable gas analyzer comprises a micro gas chromatograph (micro GC) a micro flame ionization detector (micro FID), an electrolyzer capable of electrolyzing water. The micro GC, the micro FID, and the electrolyzer are integrated into a single enclosed housing and the micro FID contains a flame-shaped electrode.

Figure 5:
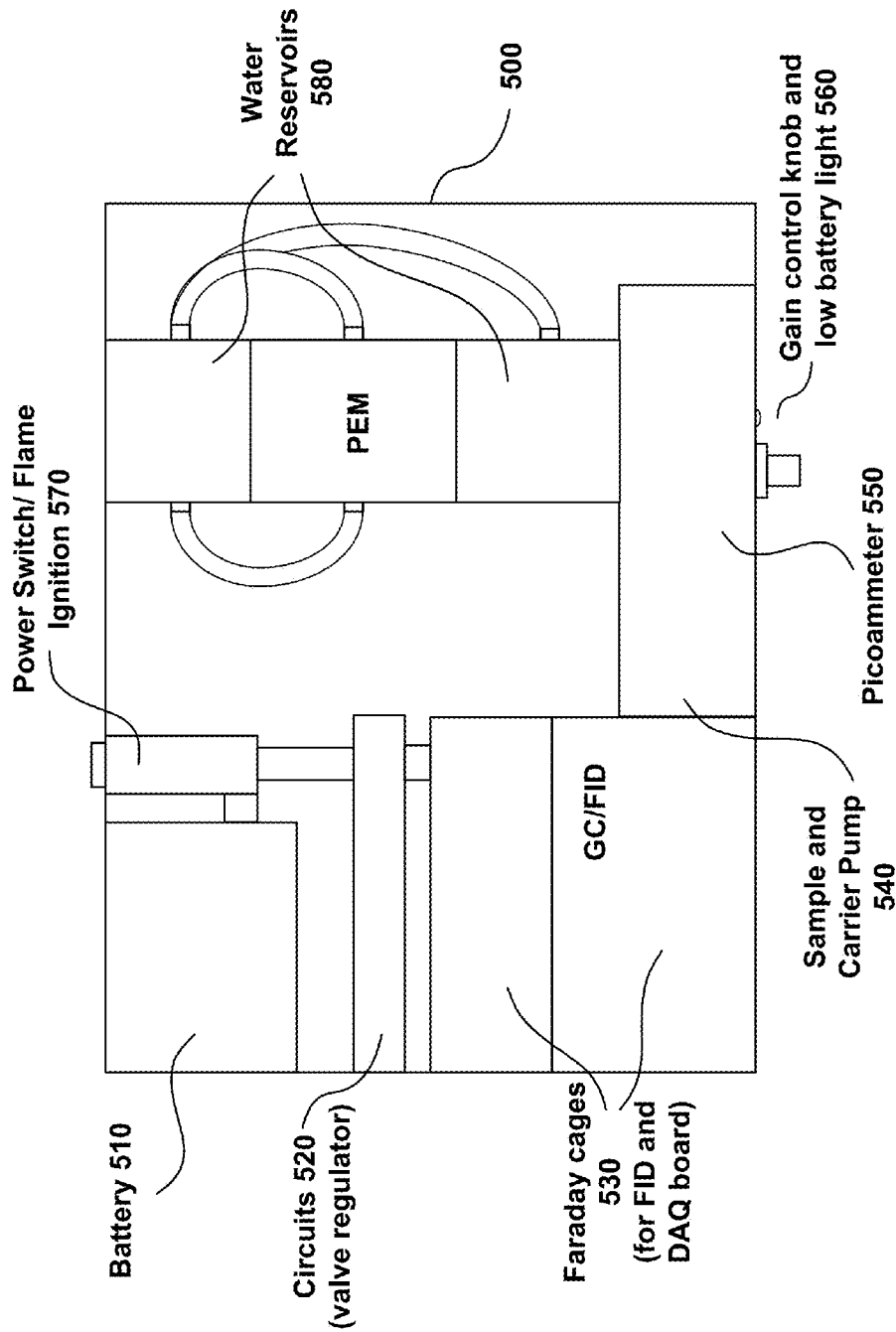
FIG. 5 shows a configuration of an exemplary portable gas analyzer.

FIG. 5 depicts a typical configuration of the portable gas analyzer ("PGA"). The PGA (500) can comprise a battery (510), circuits comprising microelectromechanical (MEMS) valves and regulators (520), Faraday cages (530), sample and carrier pump (540), picoammeter (550), gain control knob and low battery light (560), power switch and flame ignition switch (570), and water reservoirs (580) included in a polymer electrolyte membrane (PEM) electrolyzer.

In one embodiment, all of the components of the portable gas analyzer, including the micro FID, micro GC, electrolyzer, etc. are integrated into a single housing, that may be, for example, the size of a typical lunchbox. In one embodiment, the portable gas analyzer has a length from about 16 to 24 cm, a width from about 12 to 20 cm, and a height of about 6 to 10 cm. In some embodiments, the portable gas analyzer has a mass of less than 10 kg, less than 8 kg, less than 6 kg, less than 4 kg, or less than 2 kg. In one embodiment, the portable gas analyzer has a mass of 4 kg. As used herein, the term "lunchbox" may be used to refer to a portable gas analyzer, such as one or more of the embodiments described herein.

In some embodiments, the PGA optionally has a display (e.g. a five inch display) to show users the spectrum of the detected gas samples. In some embodiments, the PGA contains a USB port. Data can be downloaded using the USB port, which can be located at any convenient position in the PGA, for example at the front side of the PGA. In one embodiment, the PGA contains a user-adjustable control on the surface of the PGA. The control can be, for example, a rotatable knob. In one embodiment, the control can be used to regulate a potentiometer control to adjust the voltage that goes to the electrolyzer. In one embodiment, the PGA contains a rechargeable Li-ion battery that provides power to all the units inside the PGA, such as the water electrolyzer and valve/flame bias circuits. Any kind of Li-ion battery can be used that is not inconsistent with the objectives of the present invention, and such batteries are readily available from a variety of commercial sources. In one embodiment, the Li-ion battery is a 3.7V 15600 mAh rechargeable battery.

In one embodiment, the water electrolyzer generates the hydrogen and oxygen needed to sustain the flame inside the micro-FID. The resulting gases from the electrolyzer typically contain moisture and need to be dried by passing through drying units. In one embodiment, the PGA contains a valve/flame bias circuit that provides a train of voltages to control the microvalve as well as a DC bias across the flame of the micro-FID via the FID package. A picoammeter amplifies the collected current through the electrode of the micro-FID. Finally, a data acquisition board (DAQ) processes the analog data to digital data for displaying on the display system.

I. The Micro FID

Figure 3:
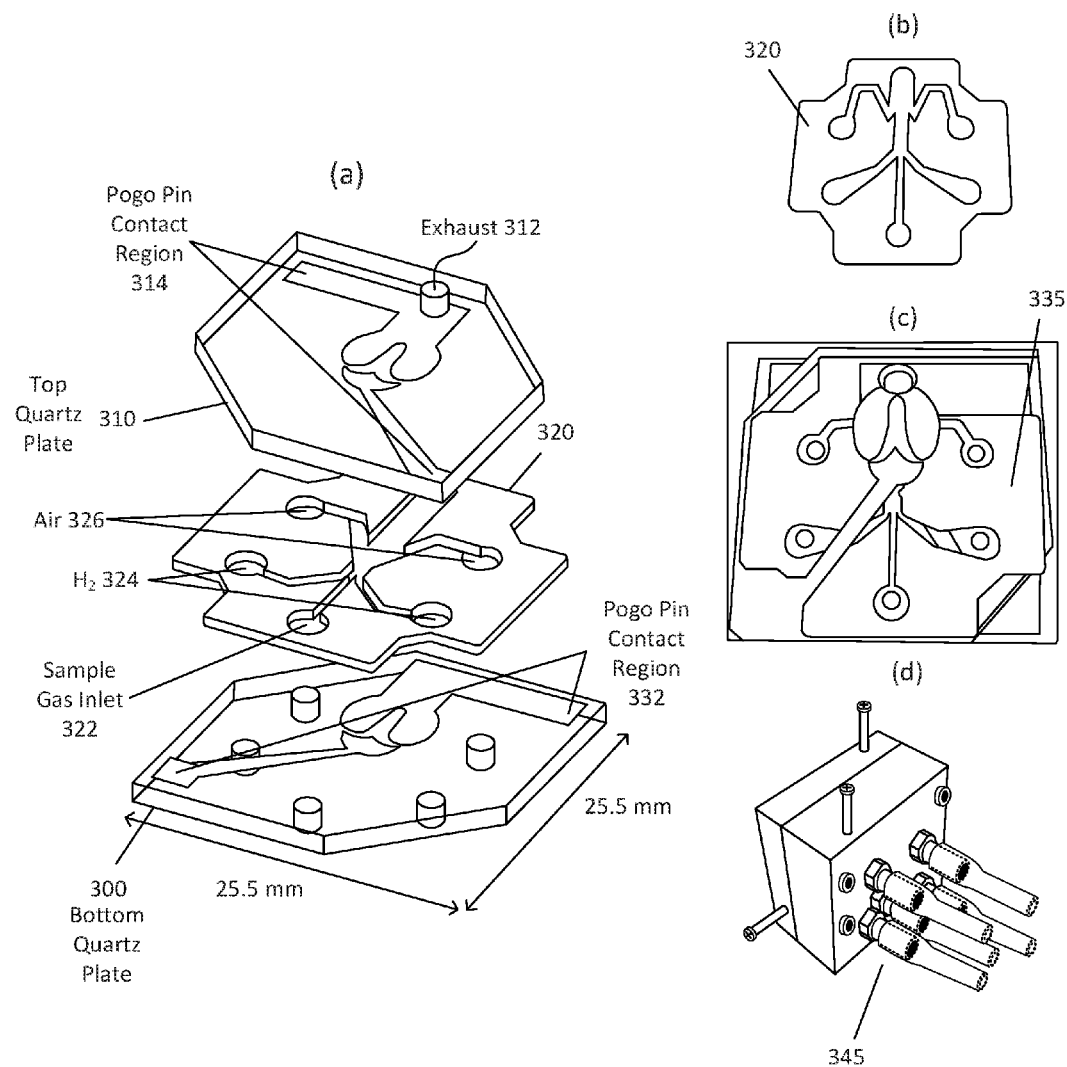
FIGS. 3(a)-(d) show a micro-flame ionization detector electrode and quartz plate stack.

An exemplary micro-FID electrode stack is depicted in FIG. 3(a). The exemplary micro-FID stack comprises a bottom quartz plate (300), top quartz plate (310), pogo contact pin region for electric current (314) and (332), Macor channel (320), sample gas inlet (322), hydrogen inlets (324), and air inlets (326).

The micro-FID stack shown in FIG. 3(a) is composed of a Macor channel and two quartz plates (1 in×1 in×0.062 in, Technical Glass Products, Painsville, Ohio). The Macor channel can be from about 400 to about 1000 µm thick. In one embodiment, the Macor channel is about 750 µm thick. In one embodiment, the channel is 500 µm thick. In some embodiments, two quartz plates are used to sandwich the channel and make an encapsulated structure to enhance the stability of the diffusion flame. The flame burns inside the enclosed space of the channel and is sustained between the quartz plates as shown in FIG. 3(a). In one embodiment, the micro-FID stack is composed of silicon. FIG. 1 shows an actual exemplary micro-FID electrode stack (100).

The top quartz plate can contain an exhaust hole 312 while the bottom quartz plate can have inlet holes to supply hydrogen, oxygen/air, and the sample gas. Air can be provided by a miniature pump and mixed with the oxygen that is generated by the electrolyzer, before the mixed gas goes into the hole. Two pairs of Cr/Au electrodes are sputtered on the quartz plates, along with the flame footprint to increase the ionization as the electrode approaches to the flame without melting of the electrodes. These electrodes create an electric field across the flame that measures the resultant ion current. FIG. 3(d) shows a Vespel™ package that holds the FID stack tightly and provide the fluidic and electrical connections. In one embodiment, the micro-FID has a 2.5×2.5×0.4 cm³ footprint.

After the desired channel shape and the flame are developed, Macor was used to machine the designed channel, although the presently disclosed embodiments are not limited to the use of Macor. Macor has low thermal expansion (93× $10^{-7}$ m/(m K)) and good stability up to temperature about 1000° C. FIG. 3(b) shows the size of the Macor channel (320) compared to a U.S. penny. FIG. 3(c) shows the assembled stack of the micro-FID (335). FIG. 3(d) shows a polyimide (Vespel) package, which holds the entire FID stack together (345). Vespel was chosen due to its good thermal characteristics, which withstand repeated heating up to about 300° C. The Vespel package includes fluidic tubes to supply the gases and holes, and pogo pins are used to supply the voltage and measure current. The position of the pogo pins attachment to the package aligns to the electric pad that is located at the end strips of the electrodes as illustrated.

Silicon channel thickness can be modified to localize the flame in the burner cavity. The Si channel can have thicknesses ranging from about 500 µm to about 1000 µm. In one embodiment, the silicon channel has a thickness of about 750 µm. The channel length from each inlet port to the burner cavity is preferable long enough to keep each flow laminar at the burner cavity. The length of the exhaust channel from the burner cavity to the exhaust hole is preferably long enough to avoid splitting of the flame. When the channel length of the exhaust channel is too short, the flame splits at the end of the channel at the exhaust hole, which can lead to loss of analytes and thus inaccurate measurements.

The silicon channels in the micro-FID can be fabricated with a variety of different angles between the hydrogen and air (or oxygen) flow channels. In one embodiment, there is a right angle between the air and hydrogen channels. In another embodiment, the air and hydrogen channels have a counter-flow configuration, where the air and hydrogen come from opposite directions. In another embodiment, there is a about a 150° angle between the hydrogen and air channels.

Figure 7:
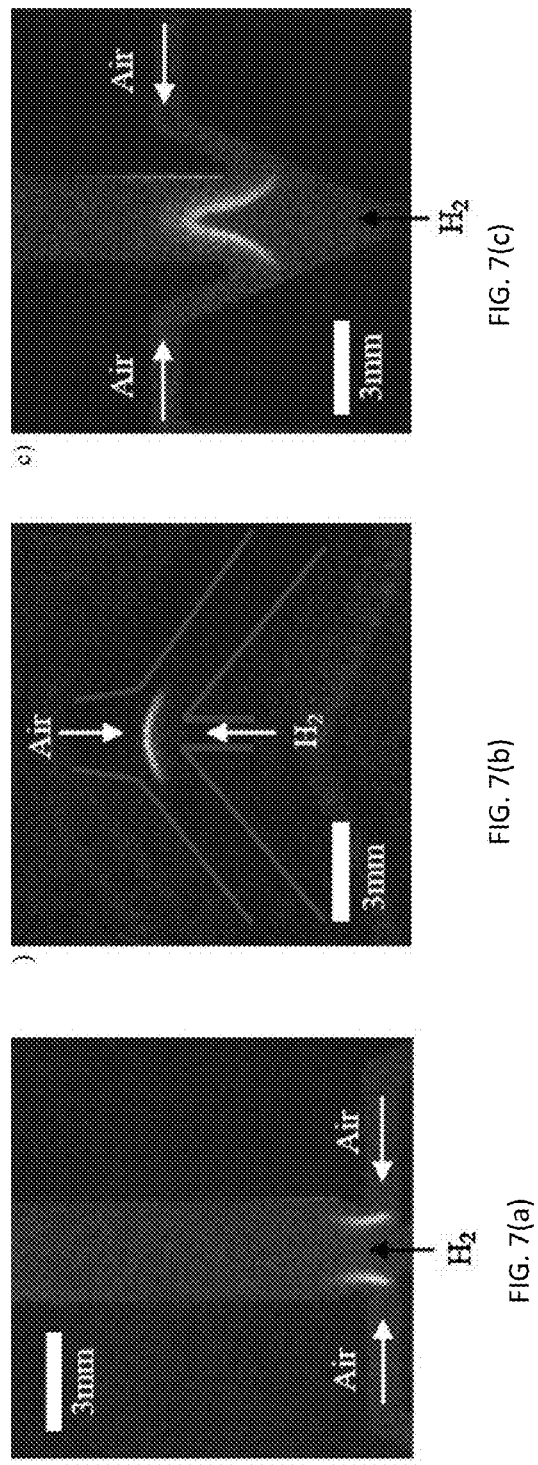
FIGS. 7(a)-(c) show representative images of a flame taken with an ICCD (Intensified Charged-Couple Device) camera.

FIG. 7(a) shows a representative image of a flame taken with an ICCD (Intensified Charged-Couple Device) camera. This flame structure is obtained by the first design and the flow rates of air and hydrogen are 40 and 80 mL/min. Two distinct flames at the left and right sides are observed. This flame structure can lead to loss of analytes due to the possible leak between two distinct flames without being ionized. Thus, this channel configuration leads to a potential loss in the signal for the micro-FID.

FIG. 7(b) shows the flame shape obtained with the second design, which is the counter-flow channel design. In this design, air comes from the top to meet the hydrogen that comes from the bottom. The flow rate is 80 mL/min for both the air and hydrogen. With this channel configuration a single flame is obtained. However this counter-flow flame design shown in FIG. 7(b) still loses analytes around the exhaust channels where the tails of the flame are extended. Part of the sample analytes can leak along the pressure gradient without being ionized.

When hydrogen and air channels meet with a 150° angle in the third design, a stable single flame is observed as shown in FIG. 7(c). This flame structure is obtained by applying air and hydrogen with the same flow rate of 80 mL/min from the side and bottom, respectively. The advantage of this folded flame design is that it can confine the analytes between the two wings. This configuration can decrease the loss of the analytes since the analyte does not have a path to leak to the exhaust without being ionized.

Computational fluid dynamics (CFD) software was used simulate the micro-flame by including the relevant physical properties with the discretized governing equations and boundary conditions. The commercial CFD software package FLUENT was used in the simulations.

FLUENT has been successfully demonstrated by other authors to accurately model micro-flame combustion. FLUENT-based simulations were used to analyze the combustion characteristics of a non-premixed hydrogen/air flame in a 3D combustor. The CFD simulations take into account phenomena such as the coupling of fluid dynamics, heat transfer, and detailed chemical kinetics. The fluid dynamics and heat transfer are simulated using the continuity, momentum, energy and species conservation equations for the combustion gases. The species transport and finite-rate chemistry are computed using the eddy dissipation-concept (EDC). The detailed chemical mechanisms are incorporated with the EDC model via GRI-1.2, which provides the reaction model for the hydrogen oxidation, and consists of 279 reactions, 31 species, and the associated Arrhenius rate constants. This combustion model is also integrated with a heat transfer model that allows us to establish thermal boundary conditions for the combustion channel within FLUENT.

The Vespel package, high temperature silicon gasket, quartz and Macor channel were modeled, and interfaces were created between the fluid and solid components to form a complete assembly. The interfaces are necessary to allow heat transfer across between the fluid and solid regions. In the model, the Vespel surfaces are exposed to ambient air, and mixed convection and radiation boundary conditions are imposed on the exposed walls. Conduction is assumed to dominate the inner solid components. The Vespel solid packaging provides significant insulation, with a low thermal conductivity of 0.35 W/m K, density of 1430 kg/m$^3$, and specific heat of 1.13 J/kg K. The emissivity and heat transfer coefficient, h, is set to establish the mixed boundary conditions for the exposed Vespel walls.

In the simulations, the Vespel emissivity is set to 0.9, and h=5.25 W/m$^2$K is used, which has been used in other microcombustion models to represents a typical free convection value. The simulation is run for the case of hydrogen, air inlet velocities of 0.95 m/s and 2 m/s respectively, and an inlet temperature of 300 K. The results of the CFD simulation are presented in FIG. 8, which shows the temperature distribution of the combustion channel.

Figure 8:
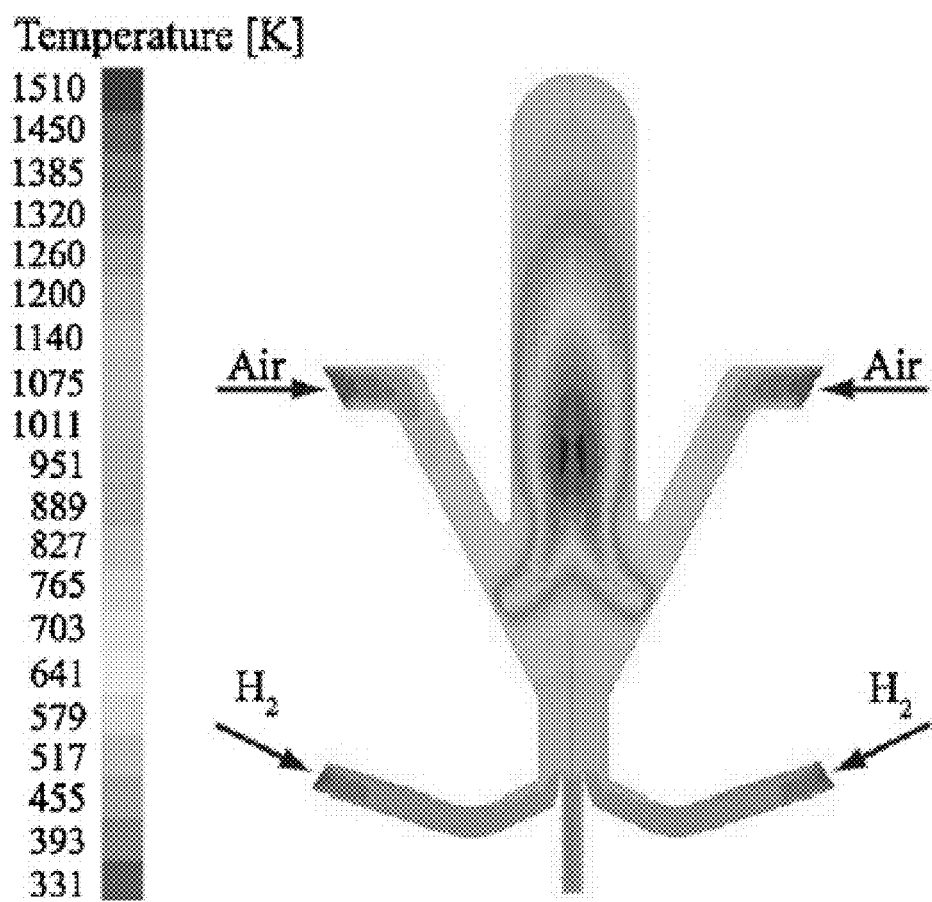
FIG. 8 shows a simulated temperature distribution of a flame channel.

The results of FIG. 8 show that the flame is shaped like a "folded" flame that contributes to the stability due to following aspects. FIG. 8 shows that the air flows through high temperature regions before reaching the combustion zone. A similar observation can be made regarding the hydrogen flow. This flow path allows for the preheating of the combustion gases, which can aid flame stability. The importance of combustion preheating in maintaining flame stability in microcombustion has been discussed by several researchers. For example, preheating of fuel and air has been shown to be important for flame ignition. Furthermore, mechanisms that facilitate heat transfer to the combustion gases are also important for maintaining flame stability. Beyond stability, even more dramatic flame blowout can occur if preheating insufficient to sustain ignition or a stable flame. The low thermal conductivity of the Vespel package is important in maintaining a stable flame by limiting heat transfer away from the combustion zone through the walls.

It is also clear from FIG. 8 that there is an extended high temperature zone established by the folded flame geometry. The high temperature region is shown in FIG. 8 to be stretched throughout the channel. Species that enter the channel from the bottom have to traverse this long high temperature region. Thus, the disclosed flame geometry can produce an enhanced response signal that corresponds to the extended temperature region that results from this folded flame structure.

The micro-FID can be manufactured in a variety of ways by those of skill in the art, and the examples set forth herein are not intended to be limiting. The silicon channels can be fabricated using a, for example, 750 μm thick (1 0 0) silicon wafer. Both sides of the wafer were spin coated with AZ4620 photoresist (PR) and exposed using a mask aligner. After the exposure, the entire wafer was developed in a solution of AZ 400K developer and deionized water (DI) water mixed with a ratio of 1:4. After the wafer is rinsed with DI water and dried, the wafer was etched with an inductively coupled plasma-deep reactive ion etcher (ICP-DRIE) using the Bosch process. Once the silicon channel was etched, the wafer was dipped into the 400T PR stripper. Before growing an oxide layer for the electrical insulation layer the silicon channels were cleaned using the SC-1 cleaning process. After the cleaning procedure the silicon channels were loaded into a thermal oxidation tube furnace to grow 5000 Å of oxide on the silicon channels.

In order to fabricate the electrodes on the quartz plates, the quartz plates were spin-coated with AZ1518 PR and exposed in a flood exposure with the electrode patterns on the quartz plates. Then, the PR pattern on quartz plates were developed in a chemical mixture of DI water and AZ 400 K developer mixed with a 4:1 ratio. After subjecting the wafer to the descum cleaning process using oxygen plasma, Cr/Au was sputtered to a thickness of 100 Å and 1000 Å respectively. In order to obtain the final electrode patterns the quartz plates were dipped into 1165 PR stripper to lift-off unnecessary PR, subjected to ultrasound, and cleaned.

II. The Micro Fid Electrode

The micro FID contains a flame-shaped electrode that dramatically improves the ionization efficiency in the micro FID and contributes to the high sensitivity of the detector. By "flame-shaped" it is meant that a squeezed folded flame is generated whose base that has two anchor points is wider than the tip of the flame where a gradual taper from the base ends with the folded shape. In order to enhance the ionization, the Cr/Au electrode pattern on the both quartz plates is made to be as close to the "folded" flame as possible so that the ionization can be maximized without melting the electrode. By using two entirely—Au sputtered quartz plates, the flame melts the Au and its melted footprint can conform to the flame shape that is employed for designing the electrode pattern.

Figure 9:
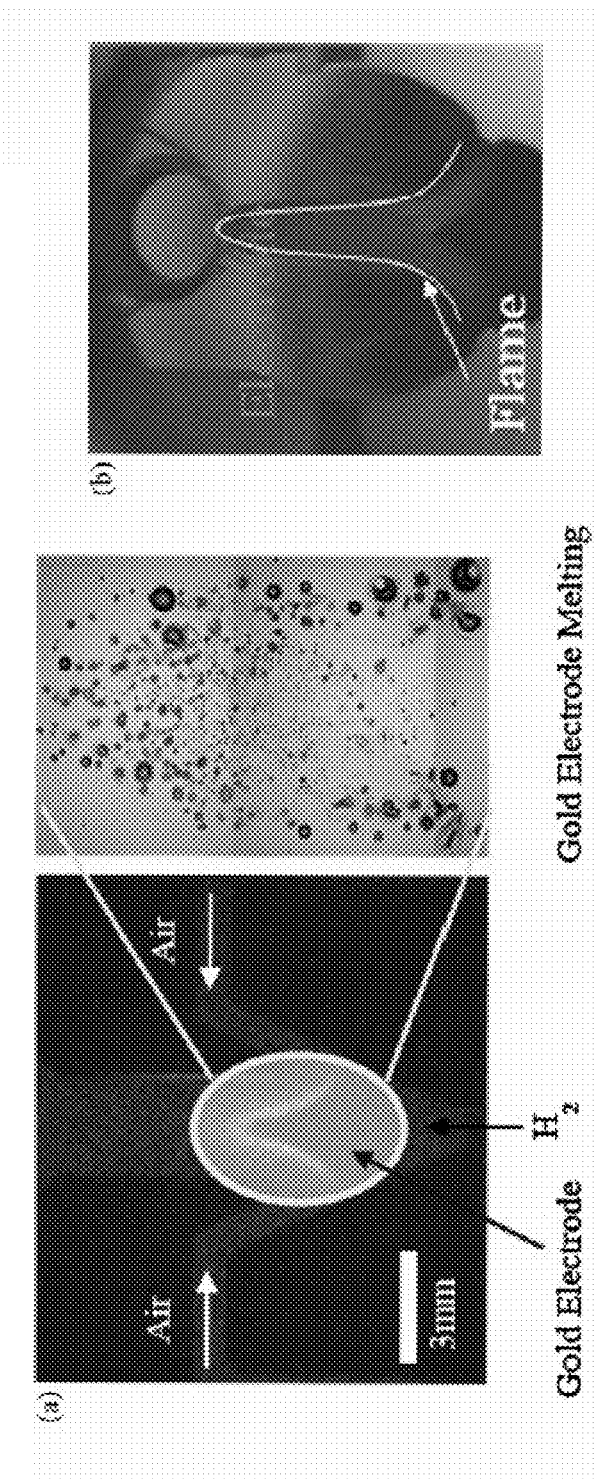
FIGS. 9(a)-(b) show the shape of a flame-shaped electrode conforming to the shape of a flame in a micro-FID.

In one embodiment, the dimensions of the flame-shaped electrode substantially conform to dimensions of a flame in provided by the micro-flame ionization detector. FIG. 9(a) illustrates that the flame generated in the micro FID can damage a plain metal electrode due to the high temperature of the local flame. The melting of the metal electrode can cause signal drift in the detector without being associated with the sample gas. To avoid melting the electrode, the electrode patterns are made as shown in FIG. 9(b), along the melted footprint in FIG. 9(a). The pattern is separated in two parts that encloses the top and bottom side of the flame as close as possible. Thus, when the flame-shaped electrode substantially conforms to the dimension of the flame, ionization of the sample can be increased without melting the electrode.

Gas sample to be eluted from the bottom port should traverse the folded-area of the flame before it burns through exhaust. Hence this folded flame structure with its electrode pattern increases residence time of the sample, thereby also increasing the ionization efficiency. The extended area of the metal electrode area surrounding the burner combustion area improves the preheating of the oxidant and fuel gas, which also contributes to flame stability. Furthermore, the two electrodes that surround the flame may be bell shaped curves, where the electrode on the inside of the flame (the hydrogen rich side) may be a smaller bell that fits inside a larger bell on the outside of the flame (the oxygen rich side). The gap between the bell curves is preferably slightly thicker than the flame thickness. For example, in some embodiments the gap between the bell curves is between about 50 and about 500 μm. This flexibility in thickness considers the variance in flame thickness when fuel and oxidant flow rates are changed.

In one embodiment, the micro flame ionization detector comprises a silicon layer.

In one embodiment, the silicon layer is from about 400 to 1000 μm thick.

In one embodiment, the silicon layer is about 750 μm thick.

In one embodiment, the silicon layer is situated between two quartz plates.

In one embodiment, at least one of the quartz plates contains an exhaust hole.

In one embodiment, the silicon layer comprises an air channel and a hydrogen channel.

In one embodiment, the angle between the air channel and the hydrogen channel is about 150°.

In one embodiment, the flame-shaped electrode is situated on both quartz plates.

III. The Micro GC

Figure 10:
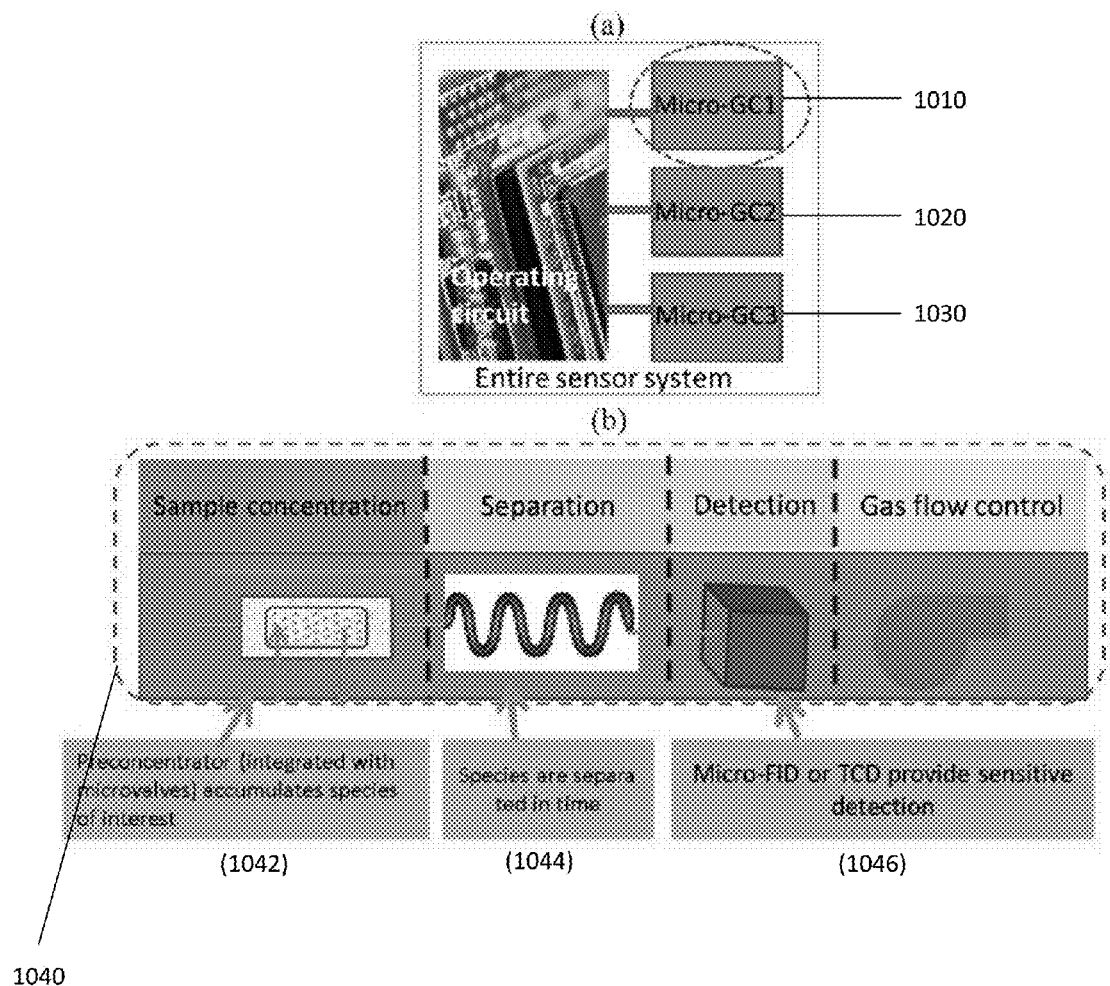
FIGS. 10(a)-(b) show a schematic of a micro-GC connected to a micro-FID.

FIG. 10 shows a schematic of a micro-GC that is connected to the micro-FID. FIG. 10(a) depicts a schematic of a system comprising three separate micro-GC units, micro-GC #1 (1010), micro-GC #2 (1020), and micro-GC #3 (1030). In one embodiment, the micro-GC comprises integrated microvalves and preconcentrator (PC) unit and a microcolumn. The PC can increase the concentration of a sample by several hundreds to thousands-fold and therefore effectively enhances the overall detection limit. The microvalves create an injection plug with a microseconds sharp band pulse to the microcolumn, which can separate compounds of interest with minimum dispersion, band broadening and tailing.

The general analytical process is depicted in FIG. 10(b) (1040). Species are accumulated in a preconcentrator system (1042), separated in time by the use of a micro-GC (1044), and detected in a micro-GC or micro-TCD (1046).

In one embodiment, the micro gas chromatograph comprises a microcolumn having a silicon substrate.

In one embodiment, the micro gas chromatograph comprises a preconcentrator.

In one embodiment, the microcolumn comprises a fusion bonded silicon substrate.

In one embodiment, the fusion bonded silicon substrate comprises two fused silicon plates.

Most of the microfabricated GC columns reported are made by fabricating a channel in silicon and capping the channel with a Pyrex® lid via anodic bonding, which can cause non-uniform temperature profiles in the channel. Replacement of the Pyrex® lid with silicon is beneficial because: (1) silicon has lower thermal mass than Pyrex®, which means the temperature programming is faster and heating power consumption is lower than those of Si-Pyrex microcolumns, and 2) easier passivation of the silicon surface compared to Pyrex®, which means lower channel wall adsorption activity thereby decreasing peak tailing and broadening of polar compounds. There have been reports of silicon-silicon microcolumns using Au diffusion bonding with a Si-channel and flat mating silicon piece to cap the channel. However, the capping method in those reports limited the formed channel to have only sharp corners, where the local stationary phase coating could be thicker than in other portions of the channel, which tends to create the peak broadening effects.

Figure 14:
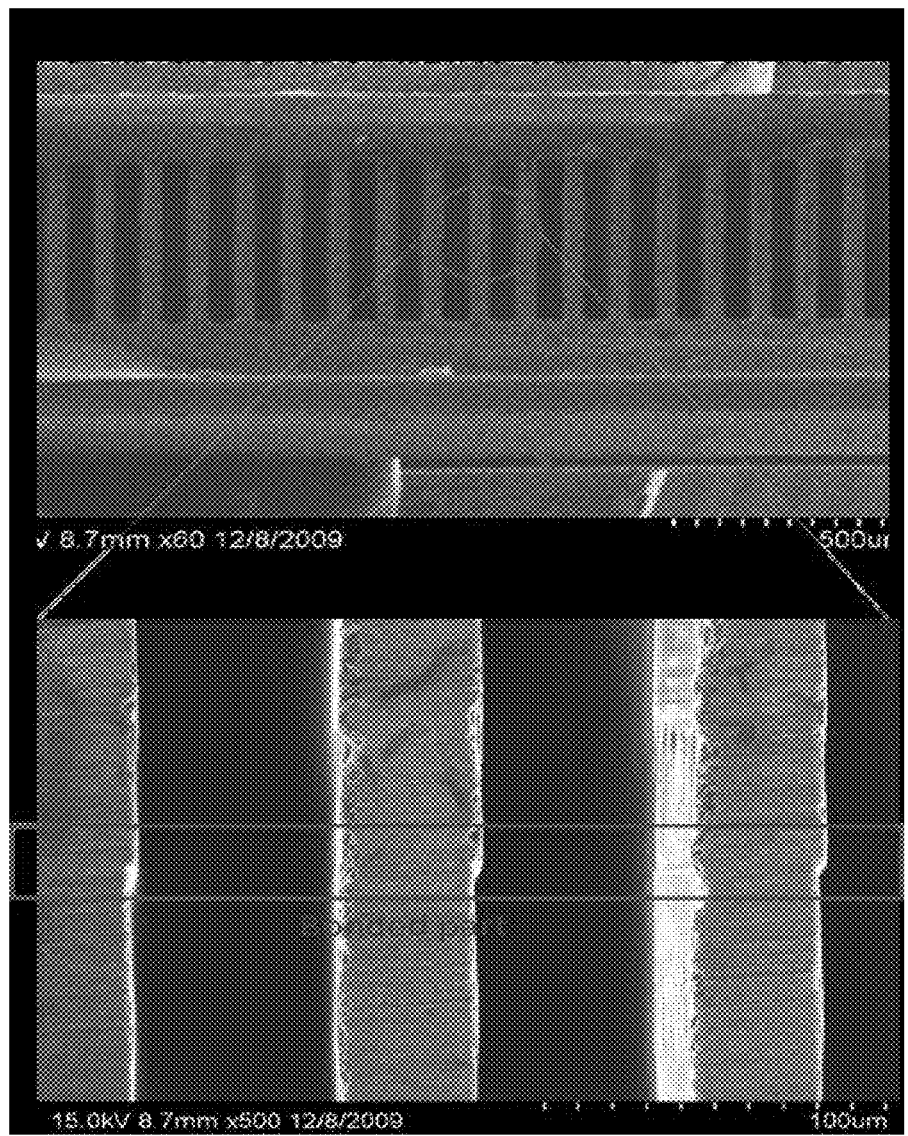
FIG. 14 shows a fusion bonded silicon microcolumn.

The provided fusion bonded silicon-silicon microcolumn allows for channels having smooth walls and corners in each microchannel before alignment and bonding so the stationary phase coating will be uniform, which avoids the peak broadening effects described above. Thus two silicon plates each have microchannels etched into them. The microchannels can have any kind of geometry for the turns and corners, including, but not limited to, straight edges, curves, serpentine, and sinusoidal geometries. FIG. 14 depicts a fusion bonded microcolumn according to one embodiment.

In some embodiments, the all-silicon microcolumn comprising two silicon plates are fusion bonded using the following process: the etched silicon plates are subjected to piranha cleaning for at least thirty minutes. Next, the surface plates are surface activated using oxygen plasma in a reactive ion etcher (RIE), which is an important step for successful bonding of the silicon plates. The fused silicon plates are finally formed by tack-bonding in an aligner having less than 2 μm accuracy, and annealing the two silicon plates at about 1100° C. for at least six hours.

In one embodiment, each of the two silicon plates contain a microchannel.

In some embodiments, the micro-GC is integrated with the detectors (e.g. micro-FID or micro-TCD) in a monolithic stack integration fashion. Monolithic stack integration is superior to a modular approach, which simply connects the separate devices in series. The advantages of monolithic integration include improvement in the portability of devices and significant reduction in dead volume is possible with this kind of direct integration, which increases the overall sensitivity of the detection system.

As used herein, "dead volume" refers to the redundant volume associated with fluidic connection between the exit of the column and the forefront of the detector. Since each unit is often running at an elevated temperature, putting all units closely together (i.e. monolithic integration) can reduce the total energy consumption. Finally, transfer lines and plumbing between devices are eliminated in the monolithic integrated device, which reduces shearing, band-broadening, and potential condensation.

Target compounds (or analytes) from the ambient environment are collected into the preconcentrator using a miniature gas pump. High surface-area adsorbents (e.g. Banasorb™) in the preconcentrator preferentially adsorb analytes from the sample stream. These analytes are later eluted into the microcolumn by rapid thermal desorption and subsequent injection enabled by flash heating and microseconds-switching valves. All of the valves' operations are conducted by multiple microvalves that are fabricated on the platform shared with the preconcentrator. Optionally, the preconcentrator microvalve stack is a component of the micro-GC, enabling the microsecond switching injection with a preconcentration factor of over a thousand fold. As shown in the exploded view of the micro-GC/FID in FIG. 11 (1100), the Si microcolumn, where the separation of the analytes takes place, is stacked with the PC-microvalve chip using a frame structure (Via frame 1) where thermal isolation is improved by an air gap. The exemplary micro-GC/micro-FID package of FIG. 11 contains the microvalve package (1110), microvalve (1120), via frame #1 (1130), micro-column (1140), via frame #2 (1150), a middle package that serves to hold the via frames (1130 and 1140) and microcolumn (1140) together as well as to align these structures to the microvalve and its package (1110), micro-FID (1170), and the micro-FID package (1180).

Prior to the monolithic stack integration, the inside of the column walls are coated with stationary phase, depending on the nature of the analyte, before being characterized. Any suitable coating may be used, including, but not limited to, non-polar coatings such as OV-1 and OV-5 and polar coatings such as OV-1701 and OV-205. In one embodiment, the via-frame is configured as in FIG. 13. In the embodiment depicted in FIG. 13, the preconcentrator/micro-GC package (1300) contains via frames (1310), a microcolumn (1320), a preconcentrator (1330), a screw (1340), a nut (1350), and a capillary or other tubing (1360).

Figure 11:
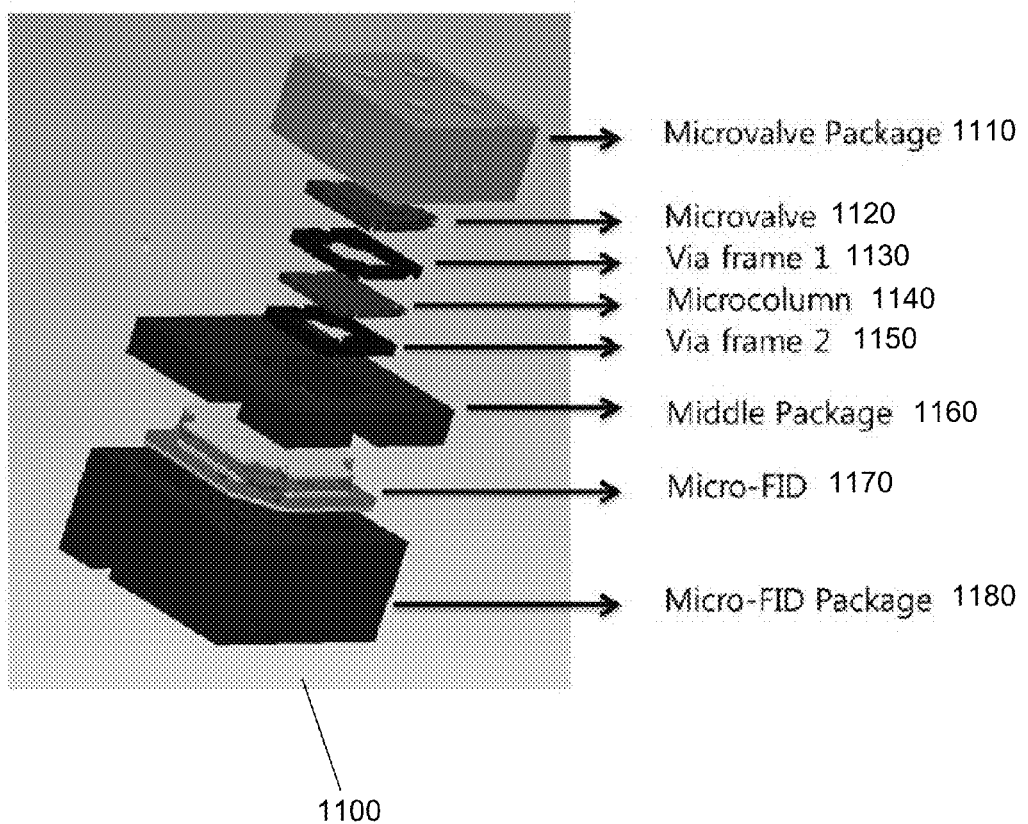
FIG. 11 shows a micro-FID and micro-GC package containing thermal isolation barriers ("via frames").

The mixture of analytes eluted into the column will, while passing through the microcolumn, be separated into a series of individual bands according to their relative affinities to the stationary phase. In the end, these individual bands of gas species at the column exit are sent to the micro-FID for detection. Another frame structure (Via frame 2 c.f. FIG. 11) is used between the microcolumn and the micro-FID to mutually thermally isolate them. The micro-GC stack is designed such that all of the fluidic connections from the micro-GC are routed to the top of the stack except the column outlet, which is connected to the injection port of the micro-FID. In one embodiment, the electrical contacts of the micro-GC are established from the top. In one embodiment, the fluidic connections of the micro-FID are established from the bottom. Electrical contacts of the micro-FID are located at the top and bottom due to the sandwich configuration of the micro-FID stack, but this minimally disturbs the other connections since the contacts are located at the outside of the micro-GC platform.

This configuration facilitates minimal interruption of the incoming gas ports and electrical contacts between the micro-GC and micro-FID. Furthermore, this stacking integration provides for ease of replacing the individual components when they need to be serviced, such that the individual components are independently replaceable. At the chip level of the monolithic integration, if a certain part malfunctions, the entire chip must be replaced. In this package level of monolithic integration, since individual components are assembled with the packages to compose the device, users have the freedom and potential cost savings of diagnosing and fixing individual components.

Stack integration of the preconcetrator, microvalve, and microcolumn (micro-GC) with the micro-TCD. The overall integration scheme of the micro-TCD to the micro-GC is basically the same as the integration scheme of the micro-FID to the micro-GC, except that the micro-TCD requires a reference gas stream from the hydrogen carrier gas. A similar configuration to FIG. 11 can be used for micro-GC/TCD integration.

In one embodiment, the PGA contains a parallel layout of the micro-GC/FID and micro-GC/TCD. In this embodiment, the operation of each GC/detector is independent, which provides users with more control and minimal conflict with other working units. Users can control the timing of sampling, desorption, an injection for each unit. Flow rates can be controlled between different units for implementing various GC testing environments in a single analysis.

IV. The Electrolyzer

Figure 15:
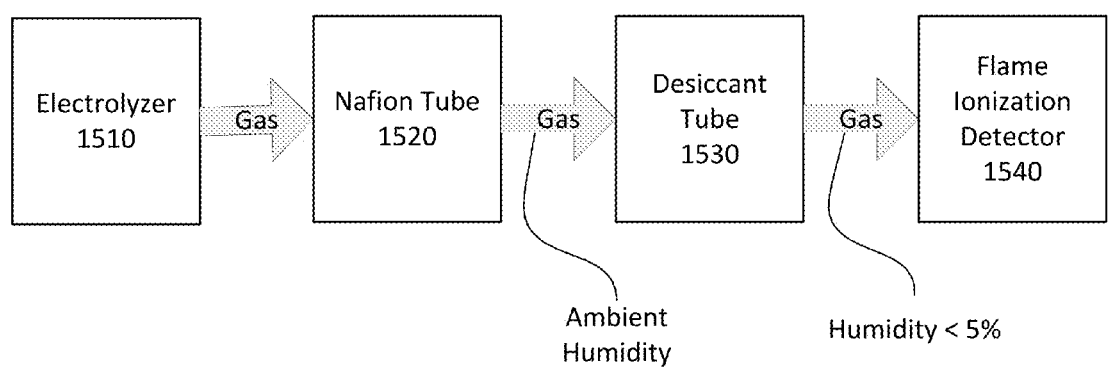
FIG. 15 shows a schematic representation of a system including an electrolyzer connected to a Nafion tube and a desiccant tube.

Any electrolyzer that is of an appropriate size and power for incorporation into the lunch box is suitable. As but one example, a commercially available electrolyzer such as the Electrolyzer 65 (h-tec, Germany), is suitable. The electrolyzer splits the water contained in a reservoir within the PGA into hydrogen and oxygen, which are fed by channels into the flame chamber. In one embodiment, as shown schematically in FIG. 15, Nafion tubes 1520 are attached to the gas outlet ports causing the water-rich oxygen and hydrogen gas produced by the electrolyzer 1510 to drop to ambient humidity. In one embodiment, the hydrogen and oxygen gas are additionally passed through a desiccant tube 1530 to reduce the humidity of the respective gases to less than 5%, less than 4%, less than 4%, or less than 2%. In one embodiment, the humidity is reduced to less than 2%.

In one embodiment, the electolyzer provides substantially all of the oxygen and hydrogen for the flame ionization detector 1540.

In one embodiment, the electrolyzer contains a plurality of gas outlet ports each connected to a desiccant tube.

In one embodiment, the desiccant tube reduces the humidity of gas from the gas outlet ports to less than 5%.

Gas drying from the eletrolyzer 1510 is made through two components that are connected in series. First one is a Nafion dryer tube 1520 which reduces humidity of the gas as similar to the ambient level. Second one is the desiccant 1530. Any solid desiccant can be used, for example, anhydrous indicating Drierite (calcium sulfate (>98%)+cobalt(II) chloride<<2%)) is used for the lunch box. Through these two drying components, it is possible to reduce the humidity of the gas below 2%. In one embodiment, 40 $cm^3$ of desiccant was used. This amount of desiccant is sufficient to dry the gases produced by the electrolyzer when the PGA is used eight hours/day for seven days. In another embodiment, 30 $cm^3$ of desiccant was used. In another embodiment, 20 $cm^3$ of desiccant was used.

V. Thermal Isolation Barrier

In certain situations, it is desirable to analyze different samples simultaneously, which often requires the use of different temperatures in adjacent micro-GC/micro-FID/micro-TCD units. In some embodiments, the PGA comprises two different integrated MEMS chips in parallel: the first MEMS chip is a micro-GC/FID combination and the second MEMS chip is a micro-GC/TCD combination. A different adsorption and separation scheme can be applied for each micro-GC module to help detect different samples. In some embodiments, the micro-GC is composed of a preconcentrator, a microvalve, and a microcolumn, all of which are stacked to minimize dead volume which can cause shearing, band broadening and tailing.

In one embodiment, the thermal isolation barrier comprises a main thermal isolation medium. In one embodiment, the thermal isolation barrier comprises two high-temperature polymerbased thermal isolation layers (e.g. Vespel) which are called "via frames". In some embodiments, one of the via frames bridges between the preconcentrator and the microcolumn, and the other bridges between the microcolumn and micro-FID. In some embodiments the via frame is hollow in the middle and supports the fluidic continuity with micro O-ring seals on both sides of the frame. Stagnant air in the middle of the via frame provides effective thermal isolation because the thermal conductivity of air is lower than that of most solid materials.

Figure 13:
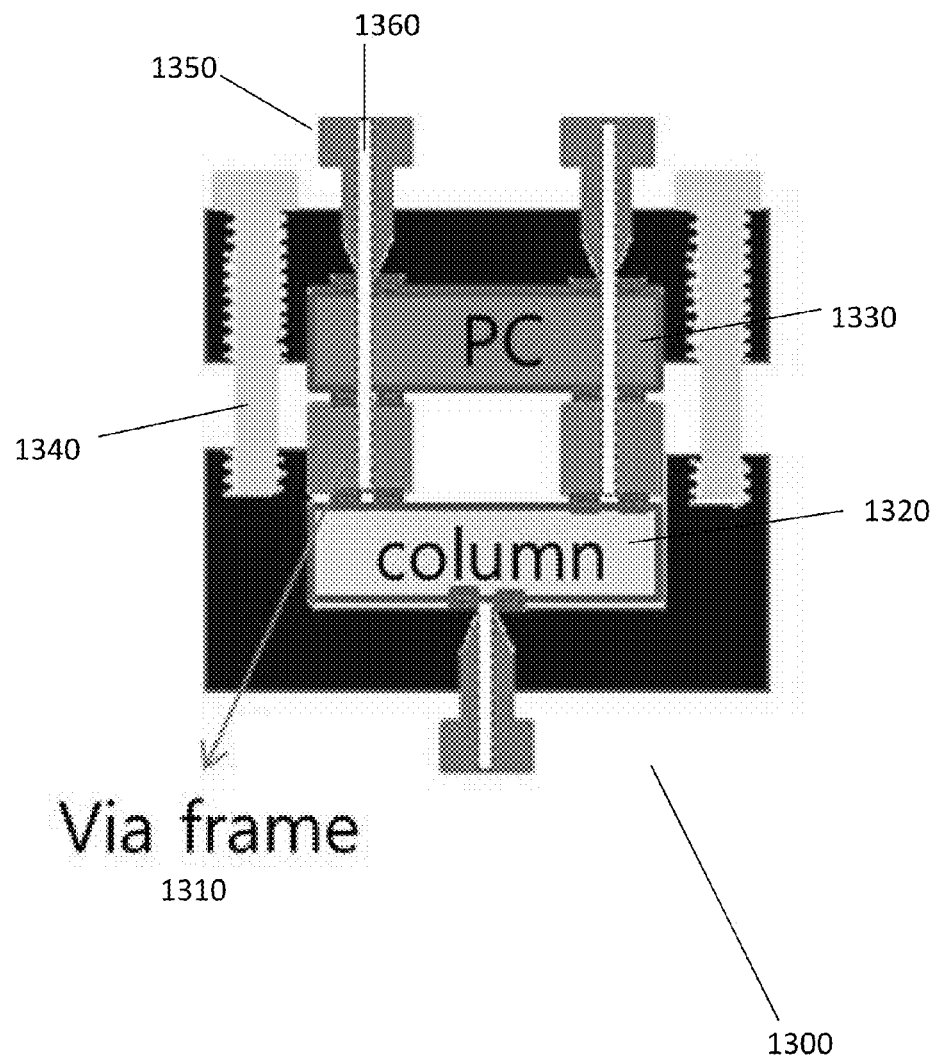
FIG. 13 shows a configuration having a preconcentrator thermally isolated from the microcolumn through a thermal isolation barrier ("via frame").

In some embodiments, the detector (e.g. micro-FID, micro-TCD, preconcentrator, micro-GC) is shielded with a thermal isolation barrier in order to maintain its operating temperature with minimal disturbance from the adjacent temperature profile of the column. In one embodiment, the micro-FID or micro-TCD will be connected to the integrated as illustrated in FIG. 13.

A thermal isolation barrier is optionally present between the micro-FID and micro-GC, since the micro-FID dissipates heat from its flame, it needs appropriate thermal isolation to the PC/valves/column stack. The micro-TCD is also sensitive to the temperature gradient between the package block and resistor filament. A stable heater is preferably utilized to keep constant heat to the package block, and the thermal isolation barrier between the block and column is preferably large enough to ensure the constant temperature of the micro-TCD package. In some embodiments, highly reflective and low emissivity metal can be coated on the thermal isolation barrier facing the side of the microcolumn, microvalve, and/or micro-FID to further enhance the thermal isolation performance.

Figure 12:
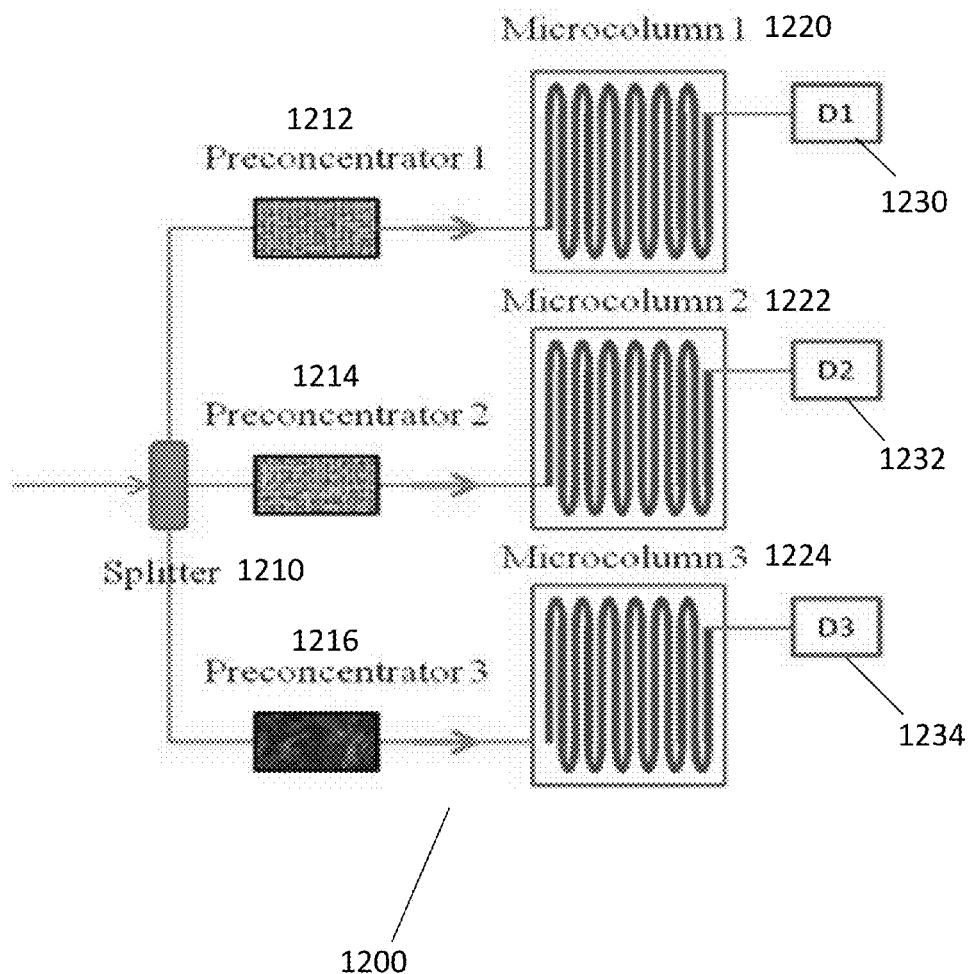
FIG. 12 shows a schematic representation of a system containing three separate and independent preconcentrator, micro-GC, and detectors.

In some embodiments, the PGA can be configured to achieve separation and detection of most SMAC-list compounds by combining two, three, or more sets of preconcentrators, microcolumns, and detectors (e.g. micro-FID, micro-TCD) in parallel. Any combination of detectors can be configured depending on the desired application. FIG. 12 illustrates a representative embodiment wherein a configuration comprising having three sets of a preconcentrators, microcolumns, and detectors in parallel (1200). Although specific column materials are discussed herein, the columns may be made from any material suitable for the particular analyte of interest. The configuration in FIG. 12 comprises a sample splitter (1210), a first preconcentrator (1212), a second preconcentrator (1214), a third preconcentrator (1216), a first microcolumn (1220), a second microcolumn (1222), a third microcolumn (1224), a first detector (1230), a second detector (1232), and a third detector (1234).

For example, Microcolumn #1 in FIG. 12 can be a packed column or porous lay open tubular (PLOT) column for light gas molecules. Low molecular weight molecules such as methane, ethane, propane, butane and carbon dioxide can be separated by using a Banasorb 30™ (Cbana Labs, Champaign, Ill.) packed column. PGA detectors according to the embodiments herein have detected nitrogen (or air), carbon monoxide, carbon dioxide, methane, octafluoropropane, trifluorobromomethane and sulfur hexafluoride using a Banasorb 22™ or 30 adsorbent packed column (with nitrogen, air, carbon monoxide to be co-eluted). In another embodiment, a MEMS Cu-PLOT containing Cu-MOF inside the microcolumn channel can be used to separate 9 gas mixtures ($CH_4$, $C_2H_4$, $C_2H_6$, $C_3H_8$, $C_4H_{10}$, $CH_3Cl$, $CH_3Br$, vinyl chloride, and 1,3-budatidene). The adsorbent in preconcentrator #1 is capable of adsorbing low molecular weight molecules.

Detector #1 in FIG. 12 is connected to the outlet of microclumn #1, and can be a micro-TCD or micro-FID to detect the heavier gases and low molecular weight gasses gases. Non-limiting examples of heavier (high molecular weight) gases include heavy aliphatic and aromatic hydrocarbons. Non-limiting examples of low molecular weight gases include $O_2$, $H_2O$, CO, $CO_2$, $NO_x$, and C1-C3 hydrocarbons. In one embodiment, microcolumn #2 is coated with, for example, a nonpolar stationary phase such as OV-1 or OV-5 to enhance the separation of nonpolar contaminants. In one embodiment, microcolumn #3 is coated with, for example, a polar stationary phase such as OV-215 or OV-1701 to separate polar contaminants. The column geometry of microcolumn #2 and #3, such as length and hydraulic diameter of the column can be optimized to handle more capacity to separate the compounds. The coating thickness of the stationary phase can also be tuned to achieve the best resolution. Detectors #2 and #3 can be micro-TCD and micro-FID or vice versa.

In one embodiment a portable gas analyzer is provided. The portable gas analyzer system comprises a micro gas chromatograph, a micro flame ionization detector, at least one thermal isolation barrier disposed between the chromatograph and the ionization detector, and a water electrolyzer.

In one embodiment, the isolation barrier comprises a high-temperature polymer. Non-limiting examples of high-temperature polymers include Vespet, polyetherimide, PEEK, Ultem, and Kapton.

In one embodiment, the isolation barrier includes a hollow chamber.

In one embodiment, the hollow chamber is filled with air.

In one embodiment, the hollow chamber is coated with a reflective metal. Non-limiting examples of reflective metals include unoxidized aluminum, tantalum, and silver.

In one embodiment, the ionization detector contains a flame-shaped electrode.

In one embodiment, the isolation barrier comprises a frame structure support structure.

In one embodiment, the isolation barrier comprises one or more fluid ports.

In one embodiment, the system includes an additional component comprising at least one of a micro-flame ionization detector, a micro gas chromatograph, or a micro thermal conductivity detector, wherein the at least one additional component is separated from the flame ionization detector or gas chromatograph by the at least one thermal isolation barrier, and wherein the at least one additional component is independently replaceable. The monolithic integration of the PGA components allows for the various detectors or GC components to be independently replaced without disturbing the remaining components or adversely affecting device operation.

In one embodiment, a method of analyzing gas is provided. The method of analyzing gas comprises providing a sample of gas, injecting the sample of gas into a portable gas analyzer, wherein the portable gas analyzer comprises: a micro gas chromatograph, a micro flame ionization detector, a flame-shaped electrode in the micro flame ionization detector, a water electrolyzer, separating the sample of gas into analyzable portions, ionizing the analyzable portions in the ionization detector with the flame-shaped electrode, and obtaining analysis results.

VI. Device Performance

Sensitivity tests were performed to evaluate the sensitivity of the PGA compared other micro-FIDs in the literature. A GC injector (Agilent GC 7890A) was used instead of the microvalves to inject a precise liquid hexane sample through a 1 meter long OV-5 coated capillary column to the PGA. This capillary column temporarily replaces the microcolumn for the compounds separation. The carrier gas was 0.3 sccm of helium. The micro-FID uses hydrogen and oxygen from the electrolyzer at 22.94 and 11.47 sccm, respectively.

Figure 2:
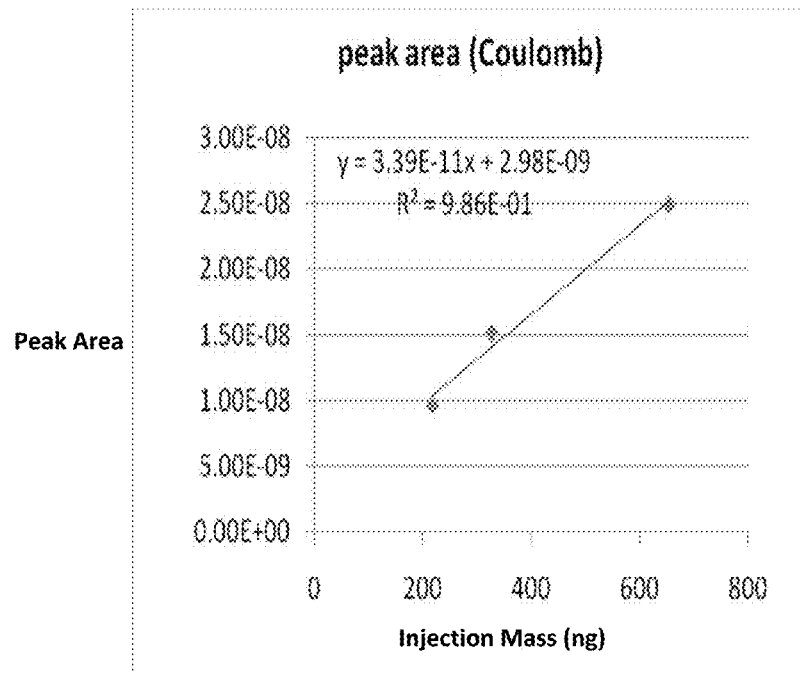
FIG. 2 shows a linear relationship between the peak area and injection mass for an exemplary analyzer.

An air pump provided 36 sccm to be mixed with the oxygen in the downstream before the micro-FID. The gain of the picoammeter is set to $10^7$. FIG. 2 shows a linear relationship between the peak area and injection mass. The table below the graph in FIG. 2 summarizes the peak voltage and area for each injection mass (hexane). The slope of the plot is the sensitivity of the micro-FID, which is 40 mC/gC. This value is more than two times higher than any other published micro-FID in the literature. In some embodiments, the sensitivity of the micro-FID in the PGA is between about 20 mC/gC and about 40 mC/gC. In some embodiments, the sensitivity of the micro-FID in the PGA is between about 25 mC/gC and about 40 mC/gC. In some embodiments, the sensitivity of the micro-FID in the PGA is between about 30 mC/gC and about 40 mC/gC. In some embodiments, the sensitivity of the micro-FID in the PGA is between about 35 mC/gC and about 840 mC/gC. In some embodiments, the sensitivity of the micro-FID in the PGA is at least 840 mC/gC.

The minimum detectable level (MDL) is defined as the minimum concentration of solute passing through the detector that can be unambiguously discriminated from the noise, which is generally accepted when the signal-to-noise ratio (S/N) ratio is at least two. The MDL will be laid on the imaginary extrapolated line of the fitted line in FIG. 2 as the injection mass gets smaller. As the injection mass gets smaller, noise plays a more important role on the MDL as S/N gets smaller.

Figure 6:
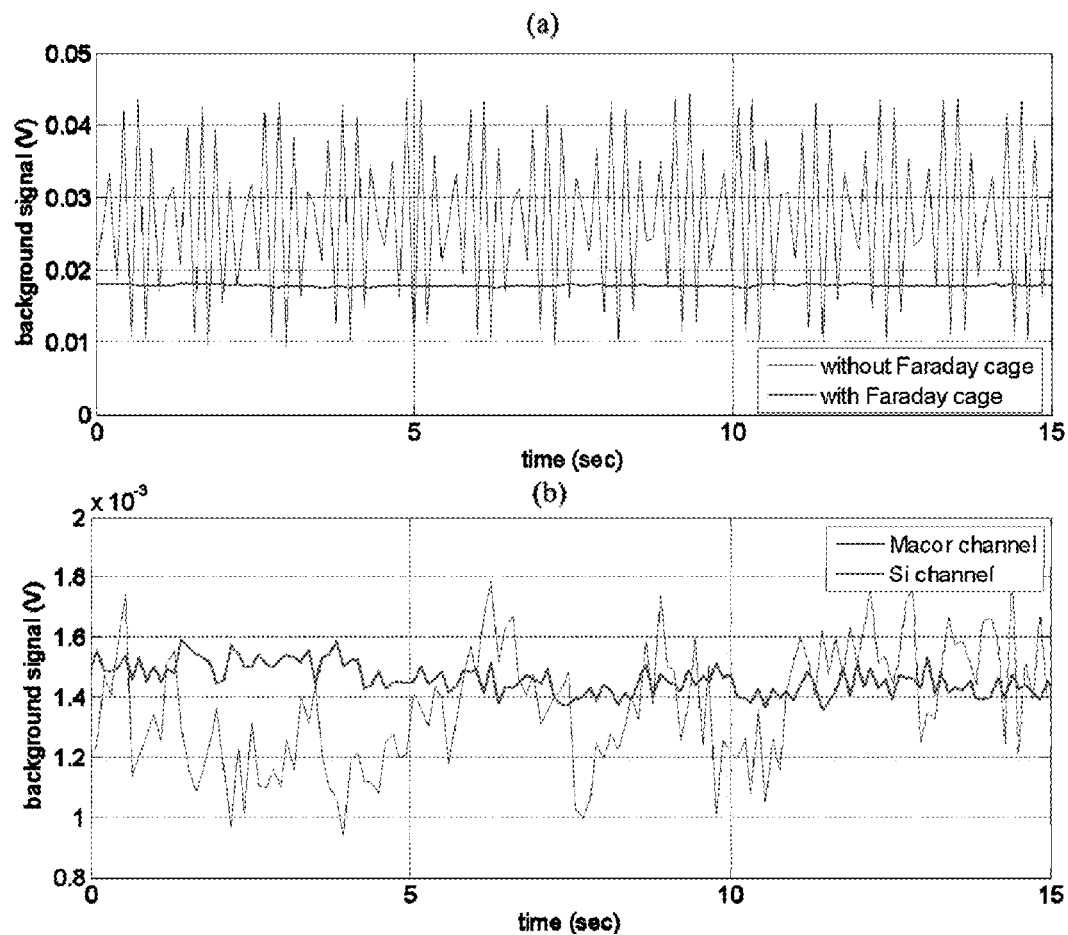
FIGS. 6(a)-(b) show comparison of signal to noise plots for an exemplary analyzer with and without a Faraday cage.

In one embodiment, a Faraday cage was used to reduce the noise of the micro-FID. Shielding and grounding of the micro-FID package with the picoammeter can be beneficial since this part is vulnerable to the signal noise and easily amplifies noise with the signal. FIG. 6(*a*) shows two background signals with and without the Faraday cage when the flame is on with the same flow conditions as in FIG. 2. The noise with the Faraday cage has been reduced more than forty-three times compared to the noise without the Faraday cage. FIG. 6(*b*) in Exhibit 1 shows the noise reduction when a Si microchannel is used versus the Macor microchannel. Both noises are tested with the Faraday cage. The silicon channel has a thermally grown $SiO_2$ layer as much as 1 μm thick on its surface for insulation. Thermal $SiO_2$ is one of the best known insulators whose melting temperature is around 1700° C. while Macor is stable up to about 1000° C. The edges of the Si wafer are also much smoother than the Macor, thereby reducing potential micro-shorts. Thus, higher leakage currents flow across the Macor, which causes a higher background noise than the Si wafer. The reduced noise level by the Faraday cage combined with the Si microchannel is less than 200 μV, which corresponds to 20 pA with the amplifier gain of $10^7$.

Figure 4:
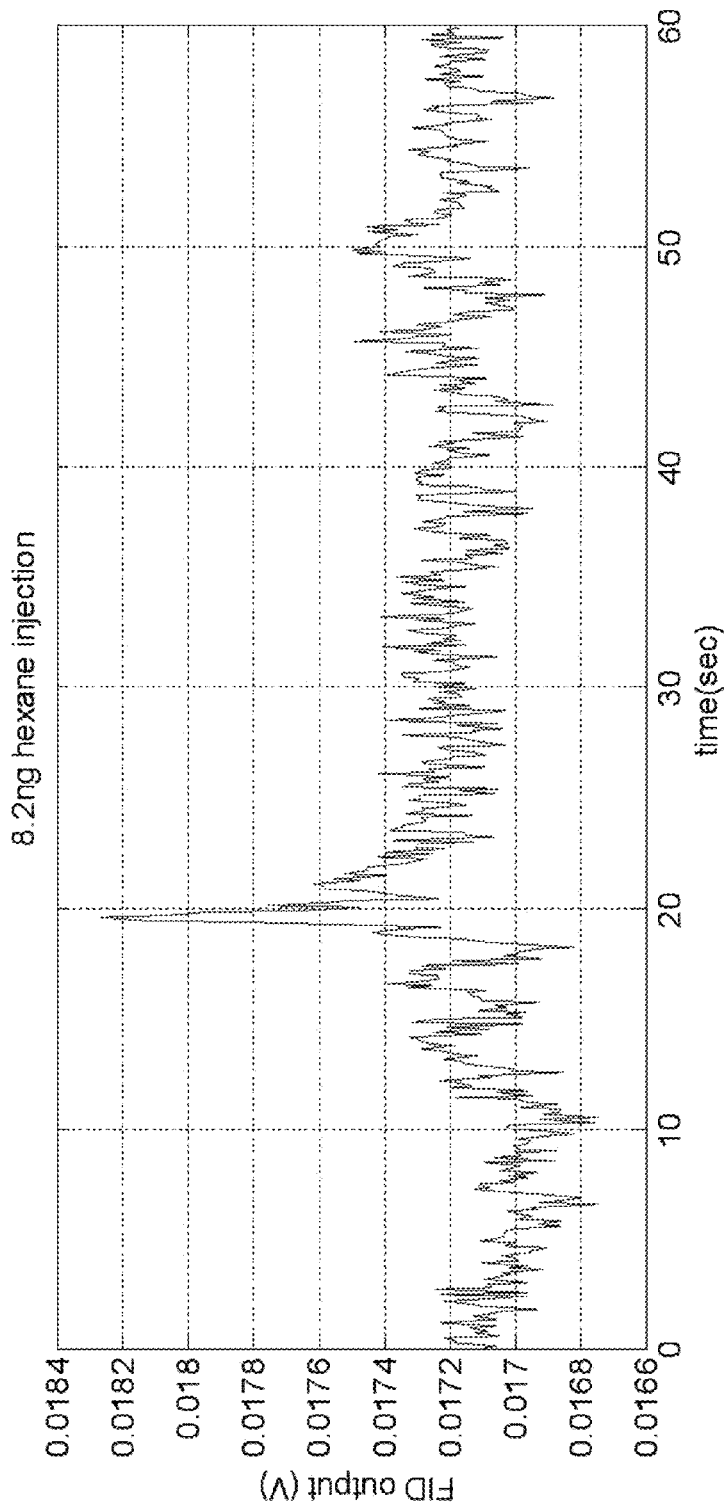
FIG. 4 show a plot of signal to noise for an 8.8 ng injection of hexane into an exemplary analyzer.

The sensitivity of the lunch box is sufficiently great to detect an injection of 8.2 ng hexane using the GC injector, as shown in FIG. 4. Considering the S/N in FIG. 4, the MDL is calculated to be about 0.65 ngC/s. In some embodiments, the sensitivity of the lunch box detector is sufficiently great to detect an injection of 0.523 ng hexane using a GC injector and the MDL at S/N=2 is about 0.083 ngC/s.

What is claimed is:

1. A portable gas analyzer system comprising:
   a micro gas chromatograph;
   a micro flame ionization detector configured to receive a sample gas from the micro gas chromatograph;
   a flame-shaped electrode in the micro flame ionization detector; and
   a water electrolyzer configured to provide at least one of oxygen and hydrogen to the micro flame ionization detector.

2. The system of claim 1, wherein the electolyzer provides substantially all of the oxygen and hydrogen for the micro flame ionization detector.

3. The system of claim 1, wherein the electrolyzer contains a plurality of gas outlet ports each connected to a desiccant tube.

4. The system of claim 3, wherein the desiccant tube reduces the humidity of gas from the gas outlet ports to less than 5%.

5. The system of claim 1, wherein the micro gas chromatograph comprises a microcolumn having a silicon substrate.

6. The system of claim 5, wherein the microcolumn comprises a fusion bonded silicon substrate.

7. The system of claim 6, wherein the fusion bonded silicon substrate comprises two fused silicon plates.

8. The system of claim 7, wherein each of the two silicon plates contain a microchannel.

9. The system of claim 1, wherein the micro gas chromatograph comprises a preconcentrator.

10. The system of claim 1, wherein the micro flame ionization detector comprises a silicon layer.

11. The system of claim 10, wherein the silicon layer is from about 400 to 1000 μm thick.

12. The system of claim 11, wherein the silicon layer is about 750 thick.

13. The system of claim 10, wherein the silicon layer is situated between two quartz plates.

14. The system of claim 13, wherein at least one of the quartz plates contains an exhaust hole.

15. The system of claim 13, wherein the flame-shaped electrode is situated on both quartz plates.

16. The system of claim 10, wherein the silicon layer comprises an air channel and a hydrogen channel.

17. The system of claim 16, wherein the angle between the air channel and the hydrogen channel is about 150°.

18. The system of claim 1, wherein dimensions of the flame-shaped electrode substantially conform to dimensions of a flame provided by the micro-flame ionization detector.

19. A gas analyzer system comprising:
   a gas chromatograph;
   a flame ionization detector configured to receive a sample gas from the gas chromatograph;
   a flame-shaped electrode included in the flame ionization detector;
   at least one thermal isolation barrier disposed between the gas chromatograph and the flame ionization detector; and
   a water electrolyzer configured to provide at least one of oxygen and hydrogen to the flame ionization detector.

20. The system of claim 19, wherein the isolation barrier comprises a high-temperature polymer.

21. The system of claim 19, wherein the isolation barrier includes a hollow chamber.

22. The system of claim 21, wherein the hollow chamber is filled with air.

23. The system of claim 21, wherein the hollow chamber is coated with a reflective metal.

24. The system of claim 19, wherein the isolation barrier comprises a frame support structure.

25. The system of claim 24, wherein the isolation barrier comprises one or more fluid ports.

26. The system of claim 19, wherein the system includes an additional component comprising at least one of a micro flame ionization detector, a micro gas chromatograph, or a micro thermal conductivity detector;
   wherein the at least one additional component is separated from the flame ionization detector or gas chromatograph by the at least one thermal isolation barrier; and
   wherein the at least one additional component is independently replaceable.

27. A method of analyzing gas comprising:
   providing a sample of
   gas into a portable gas analyzer, wherein the portable gas analyzer comprises:
      a micro gas chromatograph;
      a micro flame ionization detector connected to the micro gas chromatograph;
      a flame-shaped electrode in the micro flame ionization detector; and
      a water electrolyzer configured to provide at least one of oxygen and hydrogen to the micro flame ionization detector;
   separating the sample of gas into analyzable portions via the micro gas chromatograph;
   ionizing the analyzable portions in the micro flame ionization detector with the flame-shaped electrode; and
   obtaining analysis results.

* * * * *